(12) United States Patent
Frey et al.

(10) Patent No.: US 8,796,486 B2
(45) Date of Patent: Aug. 5, 2014

(54) PROCESS FOR AFTERTREATING POLYOLESTERS

(75) Inventors: Guido D. Frey, Riedstadt (DE); Heyko Jürgen Schultz, Bottrop (DE); Heinz Strutz, Moers (DE)

(73) Assignee: Oxea GmbH, Oberhausen (DE)

( * ) Notice: Subject to any disclaimer, the term of this patent is extended or adjusted under 35 U.S.C. 154(b) by 0 days.

(21) Appl. No.: 13/805,693

(22) PCT Filed: Jun. 29, 2011

(86) PCT No.: PCT/EP2011/003206
§ 371 (c)(1),
(2), (4) Date: Dec. 20, 2012

(87) PCT Pub. No.: WO2012/019670
PCT Pub. Date: Feb. 16, 2012

(65) Prior Publication Data
US 2013/0116467 A1  May 9, 2013

(30) Foreign Application Priority Data

Jul. 17, 2010 (DE) .......................... 10 2010 027 458

(51) Int. Cl.
*C07C 69/34* (2006.01)
*C07C 69/52* (2006.01)
*C07C 67/60* (2006.01)

(52) U.S. Cl.
CPC ...................................... *C07C 67/60* (2013.01)
USPC ........................................................ 560/198

(58) Field of Classification Search
USPC ......................................... 560/198, 204, 191
See application file for complete search history.

(56) References Cited

U.S. PATENT DOCUMENTS 2,628,249 A * 2/1953 Bruno, Jr. ....................... 560/98
2,957,023 A * 10/1960 Dimler, Jr. et al. ............. 560/98
3,043,872 A * 7/1962 Roberts et al. ................ 562/593
3,891,694 A * 6/1975 Mills et al. ..................... 560/78
5,324,853 A * 6/1994 Jones et al. ..................... 560/98

FOREIGN PATENT DOCUMENTS

| DE | 62047 | * | 6/1968 |
| DE | 197 41 913 C1 | | 12/1998 |
| EP | 2 308 821 A2 | | 4/2011 |
| EP | 2 308 822 A2 | | 4/2011 |

OTHER PUBLICATIONS

Dow (downloaded from the internet Oct. 28, 2013, 2007).*
Zwintzscher et al. (DD patent 62047, 1967, English translation by Phoenix Translations, Nov. 2013).*
The Analyst, Green Supplement, (2008).*
International Search Report.
International Preliminary Report on Patentability.

* cited by examiner

*Primary Examiner* — Brandon Fetterolf
*Assistant Examiner* — Blaine G Doletski
(74) *Attorney, Agent, or Firm* — Michael W. Ferrell

(57) ABSTRACT

A process for aftertreatment of polyol esters prepared by reacting polyols of the general formula $$H-(-O-[-CR^1R^2-]_m-)_o-OH$$

in which $R^1$ and $R^2$ are each independently hydrogen, an alkyl radical having 1 to 5 carbon atoms, or a hydroxyalkyl radical having 1 to 5 carbon atoms, m is an integer of 1 to 10, o is an integer of 2 to 15, with linear or branched aliphatic monocarboxylic acids having 3 to 20 carbon atoms in the presence of an adsorbent and in the presence of metal compounds selected from the group of titanium compounds, zirconium compounds, tin compounds, zinc compounds, iron compounds and aluminum compounds as a catalyst while removing the water formed and subsequently treating with steam, characterized in that the polyol ester obtained is aftertreated first with an oxidizing or reducing compound and immediately thereafter with steam at a temperature of 150 to 250° C. and over a period of 0.5 to 5 hours.

21 Claims, No Drawings

PROCESS FOR AFTERTREATING POLYOLESTERS

CLAIM FOR PRIORITY

This application is a national phase application of PCT/EP2011/003206 FILED Jun. 29, 2011 which was based on application DE 102010027458 filed Jul. 17, 2010. The priorities of PCT/EP2011/003206 and DE 102010027458 are hereby claimed and their disclosures incorporated herein by reference.

TECHNICAL FIELD

The invention relates to a process for aftertreatment of polyol esters prepared by reaction of linear or branched aliphatic monocarboxylic acids having 3 to 20 carbon atoms with polyols in the presence of an adsorbent and in the presence of metal compounds as catalysts, by aftertreatment with oxidizing or reducing compounds and immediately thereafter with steam.

BACKGROUND

Esters of polyhydric alcohols, also known as polyol esters, find a wide range of varying uses in industry, for example as plasticizers or lubricants. The selection of suitable starting materials allows the physical properties, for example boiling point or viscosity, to be controlled, and the chemical properties, such as hydrolysis resistance or stability to oxidative degradation, to be taken into account. Polyol esters can also be tailored to the solution of specific performance problems. Detailed overviews of the use of polyol esters can be found, for example, in Ullmann's Encyclopedia of Industrial Chemistry, 5th edition, 1985, VCH Verlagsgesellschaft, vol. A1, pages 305-319; 1990, vol. A15, pages 438-440, or in Kirk Othmer, Encyclopedia of Chemical Technology, 3rd edition, John Wiley & Sons, 1978, vol. 1, pages 778-787; 1981, vol. 14, pages 496-498.

The use of polyol esters as lubricants is of great industrial significance, and they are used particularly for those fields of use in which mineral oil-based lubricants only incompletely meet the requirements set. Polyol esters are used especially as turbine engine and instrument oils. Polyol esters for lubricant applications are based frequently on 1,3-propanediol, 1,3-butanediol, diethylene glycol, triethylene glycol, tetraethylene glycol, 1,2-propylene glycol or higher propylene glycols. They can be prepared in different ways. In addition to the reaction of alcohol and acid, optionally in the presence of acidic catalysts, further processes are employed in practice to obtain G esters, including the reaction of diol with acid halide, the transesterification of a carboxylic ester with a diol, and the addition of ethylene oxide onto carboxylic acids (ethoxylation). In industrial manufacture, only the direct reaction of diol and carboxylic acid and the ethoxylation of carboxylic acids have become established as production processes, preference usually being given to the esterification of diol and acid. This is because this process can be performed with no particular complexity in conventional chemical apparatus, and it affords chemically homogeneous products. Compared to this, ethoxylation requires extensive and costly technical equipment. Ethylene oxide is a very reactive chemical substance. It can polymerize explosively and forms explosive mixtures with air within very wide mixing ranges. Ethylene oxide irritates the eyes and the respiratory tract, leads to chemical burns and to liver and kidney damage, and is carcinogenic. The handling thereof therefore entails extensive safety measures. Moreover, scrupulous cleanliness of storage apparatus and reaction apparatus has to be ensured, in order to rule out the formation of undesired impurities as a result of side reactions of the ethylene oxide with extraneous substances. Finally, the reaction with ethylene oxide is not very selective, since it leads to mixtures of compounds of different chain length.

The direct esterification of alcohols with carboxylic acids is one of the basic operations in organic chemistry. In order to increase the reaction rate, the conversion is typically performed in the presence of catalysts. The use of one of the reactants in excess and/or the removal of the water formed in the course of the reaction ensures that the equilibrium is shifted in accordance with the law of mass action to the side of the reaction product, i.e. of the ester, which means that high yields are achieved.

Comprehensive information regarding the preparation of esters of polyhydric alcohols, also including esters of ethylene glycols and fatty acids, and regarding the properties of selected representatives of these compound classes can be found in Goldsmith, Polyhydric Alcohol Esters of Fatty Acids, Chem. Rev. 33, 257 ff. (1943). For example, esters of diethylene glycol, of triethylene glycol and of polyethylene glycol are prepared at temperatures of 130 to 230° C. over reaction times of 2.5 to 8 hours. To remove the water of reaction, carbon dioxide is used. Suitable catalysts mentioned for the esterification of polyhydric alcohols are inorganic acids, acidic salts, organic sulphonic acids, acetyl chloride, metals or amphoteric metal oxides. The water of reaction is removed with the aid of an entraining agent, for example toluene or xylene, or by introducing inert gases such as carbon dioxide or nitrogen.

The production and the properties of fatty acid esters of the polyethylene glycols are discussed by Johnson (edit.), Fatty Acids in Industry (1989) Chapter 9, Polyoxyethylene Esters of Fatty Acids, and a series of preparative hints are given. Higher diester concentrations are achieved by the increase in the molar ratio of carboxylic acid to glycol. Suitable measures for removing the water of reaction are azeotropic distillation in the presence of a water-immiscible solvent, heating while passing through an inert gas, or performing the reaction under reduced pressure in the presence of a desiccant. When the addition of catalysts is dispensed with, longer reaction times and higher reaction temperatures are required. Both reaction conditions can be made milder by the use of catalysts. In addition to sulphuric acid, organic acids such as p-toluenesulphonic acid and cation exchangers of the polystyrene type are the preferred catalysts. The use of metal powders, such as tin or iron, is also described. According to the teaching from U.S. Pat. No. 2,628,249, colour problems in the case of catalysis with sulphuric acid or sulphonic acid can be alleviated when working in the presence of activated carbon.

Further metallic catalysts used to prepare polyol esters are also alkoxylates, carboxylates or chelates of titanium, zirconium or tin, for example according to U.S. Pat. No. 5,324,853 A1. Such metal catalysts can be considered as high-temperature catalysts, since they achieve their full activity only at high esterification temperatures, generally above 180° C. They are frequently added not at the start of the esterification reaction, but after the reaction mixture has already been heated up and has reacted partly with elimination of water. In spite of the relatively high reaction temperatures and relatively long reaction times required compared to the conventional sulphuric acid catalysis, crude esters with a comparatively low colour number are obtained in the case of catalysis with such metal compounds. Common esterification catalysts are, for example, tetra(isopropyl) orthotitanate, tetra(butyl) orthotitanate, tetra(butyl) zirconate or tin(II) 2-ethylhexanoate.

The catalytic esterification reaction of polyols with carboxylic acids achieves, based on the component present in deficiency, a high conversion within a comparatively short time, but a comparatively long reaction time has to be accepted for the remaining conversion to the desired polyol esters. Although a procedure hydrolyses the metal compounds to insoluble solids, which can be filtered off before the further workup of the crude ester compound. According to U.S. Pat. No. 4,304,925 A1, the crude esterification product, before addition of alkali, is first admixed with water and treated under hot conditions. This converts the hydrolysed metal compounds to readily filterable precipitates.

U.S. Pat. No. 2,628,249 A discloses the esterification of ether polyols with aliphatic monocarboxylic acids. Color problems in the case of catalysis with sulphuric acid or sulphonic acids can be alleviated when the esterification is performed in the presence of activated carbon.

The prior art for preparation of polyol esters under metal catalysis requires either a special reactor design in order to complete the esterification reaction within an economically acceptable time, or an additional treatment with water under hot conditions, in order to substantially completely remove the metallic catalyst after the esterification reaction has ended with formation of hydrolysis products which can be filtered off readily.

Even though polyol esters are generally obtained with satisfactory colour number in the case of use of metallic catalysts, industrial production occasionally also gives products which do not meet the specification values with regard to colour number and acid number. While the process according to DE 10 2009 048 775 A1 enables polyol esters to be obtained in high quality in a simple manner, it is desirable to provide a process in which a simple aftertreatment affords on-spec polyol esters if the polyol esters obtained by the production process according to DE 10 2009 048 775 A1 should not have the required specification, for example due to a fault which occurs during industrial production.

EP 2 308 821 A2 discloses a process for lightening the color of polyol esters, wherein the reaction mixture, in the course of workup, after removal of unconverted starting compounds, is treated with ozone or ozone-containing gases, immediately followed without any further intervening steps by a steam treatment. The workup of the reaction mixture is conducted without adsorbents.

EP 2 308 822 A2 considers an analogous process for lightening the color of polyol esters using peroxidic compounds.

DE 27 29 627 A1 also discloses the treatment of carboxylic esters with ozone. After the ozone treatment, the reaction mixture is neutralized with an aqueous alkali solution and washed with water. Volatile constituents are subsequently driven out at elevated temperature and under reduced pressure or at standard pressure. According to the process from DD 57 596 A, aromatic dicarboxylic esters, to lighten the color, are admixed with an aqueous hydrogen peroxide solution in the presence of alkali and then subjected to a steam treatment.

DE 101 21 866 A1 discloses a transesterification process for preparing fatty acid polyol esters, which is conducted in the presence of reducing agents and alkali metal bases. The transesterification reaction may be followed by bleaching with hydrogen peroxide. DE 197 41 913 C1 proposes admixing a reaction product which is obtained by esterification of fatty acids with alcohols under $Sn^{4+}$ catalysis, in the course of workup, with a combined reducing agent and precipitant. This forms sparingly soluble $Sn^{2+}$ compounds.

It was therefore an object of the present invention to provide a process in which a simple aftertreatment can improve the quality of polyol esters already prepared and worked up under metal catalysis such that on-spec polyol esters which can be used in a wide variety of ways are obtained.

SUMMARY OF INVENTION

The invention therefore consists in a process for aftertreatment of polyol esters prepared by reacting polyols of the general formula

in which $R^1$ and $R^2$ are each independently hydrogen, an alkyl radical having 1 to 5 carbon atoms, preferably methyl, ethyl or propyl, or a hydroxyalkyl radical having 1 to 5 carbon atoms, preferably the hydroxymethyl radical, m is an integer of 1 to 10, preferably 1 to 8 and especially 1, 2, 3 or 4, o is an integer of 2 to 15, preferably 2 to 8 and especially 2, 3, 4 or 5, with linear or branched aliphatic monocarboxylic acids having 3 to 20 carbon atoms in the presence of an adsorbent and in the presence of metal compounds selected from the group of titanium compounds, zirconium compounds, tin compounds, zinc compounds, iron compounds and aluminium compounds as a catalyst while removing the water formed and subsequently treating with steam, characterized in that the polyol ester obtained is aftertreated first with an oxidizing or reducing compound and immediately thereafter with steam at a temperature of 150 to 250° C. and over a period of 0.5 to 5 hours.

DETAILED DESCRIPTION

The reaction between the polyol and aliphatic monocarboxylic acid starting compounds, depending on the starting materials, sets in within the range from about 120 to 180° C., and can subsequently be conducted to completion in different ways.

One configuration of the esterification stage involves first heating, proceeding from room temperature to a temperature up to a maximum of 280° C., preferably up to 250° C., and, with the temperature kept constant, lowering the pressure stage by stage proceeding from standard pressure, in order to facilitate the removal of the water of reaction. The selection of the pressure stages, whether one, two or more than two stages, and of the pressure to be established at a particular stage, can be varied over a wide range and matched to the particular conditions. For example, in a first stage, the pressure can be lowered proceeding from standard pressure first down to 600 hPa, and then the reaction can be conducted to completion at a pressure of 300 hPa. These pressure figures are guide values which are appropriately complied with.

In addition to the variation of the pressure, it is likewise also possible to alter the temperature in one, two or more than two stages proceeding from room temperature during the esterification reaction, such that the temperature is increased from stage to stage at constant pressure, typically up to a maximum temperature of 280° C. However, it has been found to be appropriate to heat to a maximum of 280° C. with rising temperature from stage to stage, and also to lower the pressure from stage to stage. For example, the esterification reaction can be conducted proceeding from room temperature in a first stage at a temperature up to 190° C. A reduced pressure down to 600 hPa is likewise applied, in order to accelerate the driving-out of the water of reaction. On attainment of the temperature stage of 190° C., the pressure is lowered once again down to 300 hPa, and the esterification reaction is conducted to completion at a temperature up to 250° C. These temperature and pressure figures are guide values which are appropriately complied with. The temperature and pressure conditions to be established at the particular stages, the number of stages and the particular temperature increase or pressure reduction rate per unit time can be varied over a wide range and adjusted according to the physical properties of the starting compounds and of the reaction products, the temperature and pressure conditions of the first stage being established proceeding from standard pressure and room temperature. It has been found to be particularly appropriate to increase the temperature in two stages and to reduce the pressure in two stages.

The lower limit of the pressure to be established depends on the physical properties, such as boiling points and vapour pressures, of the starting compounds and of the reaction products formed, and is also determined by the plant equipment. Proceeding from standard pressure, it is possible to work stage by stage within these limits with pressures decreasing from stage to stage. The upper temperature limit, typically 280° C., should be complied with in order to avoid the formation of decomposition products, some of which have a damaging effect on colour. The lower limit of the temperature stages is determined by the reaction rate, which must still be sufficiently high to conclude the esterification reaction within an acceptable time. Within these limits, it is possible to work stage by stage with temperatures rising from stage to stage.

The particular reaction conditions, such as temperature, reaction time, pressure to be applied or catalyst to be used, should be tailored to the particular polyol ester, in order to force the formation of colouring components into the background and as far as possible to avoid degradation reactions of the polyol ester with a sufficient reaction rate. In the case of polyol esters based on ether diols, for example triethylene glycol or tetraethylene glycol, enhanced degradation of the ether skeleton may set in when the reaction conditions, such as temperature, reaction time and type and amount of catalyst, are not adjusted in a controlled manner to the particular polyol ester.

The esterification can be undertaken with stoichiometric amounts of polyol and of aliphatic monocarboxylic acid. Preference is given, however, to allowing the polyol to react with excess monocarboxylic acid, which is generally the lower-boiling component and which can be removed by distillation in a simple manner in the subsequent workup of the crude ester. The aliphatic monocarboxylic acid is used in a 10 to 50% molar excess, preferably in a 20 to 40% molar excess, per mole of hydroxyl group to be esterified in the polyol.

The water of reaction formed is distilled out of the reaction vessel in the course of the esterification reaction together with the excess monocarboxylic acid and passed into a downstream phase separator in which monocarboxylic acid and water separate according to their solubility properties. In some cases, the monocarboxylic acid used also forms an azeotrope with water under the reaction conditions and is capable of removing the water of reaction as an entraining agent. The occurrence of water can be used to monitor the progress of the reaction. The water separated out is removed from the process, while the monocarboxylic acid flows out of the phase separator back into the reaction vessel. The addition of a further organic solvent, such as hexane, 1-hexene, cyclohexane, toluene, xylene or xylene isomer mixtures, which assumes the task of the azeotroping agent, is not ruled out, but it is restricted to a few exceptional cases. The azeotroping agent can be added as early as at the start of the esterification reaction or after the attainment of relatively high temperatures. When the theoretically expected amount of water has been obtained or the hydroxyl number, for example determined to DIN 53240, has fallen below a set value, the reaction is ended by allowing the reaction mixture to cool.

The catalysts used for the esterification of the polyol with the monocarboxylic acid are metal compounds selected from the group of titanium compounds, zirconium compounds, tin compounds, zinc compounds, iron compounds and aluminium compounds. Suitable compounds are, for example, tin(II) oxide, tin(IV) oxide, tin carboxylates such as tin(II) 2-ethylhexanoate, tin(II) oxalate, tin(II) acetate or tin(IV) acetate, tin(IV) alkoxides such as tetra(methyl) stannate, tetra (ethyl) stannate, tetra(propyl) stannate, tetra(isopropyl) stannate or tetra(isobutyl) stannate, or organotin compounds such as butyltin maleate or dibutyltin dilaurate.

The suitable titanium compounds include alkoxides such as tetra(methyl) orthotitanate, tetra(ethyl) orthotitanate, tetra (propyl) orthotitanate, tetra(isopropyl) orthotitanate, tetra (butyl) orthotitanate, tetra(isobutyl) orthotitanate, tetra(pentyl) orthotitanate or tetra(2-ethylhexyl) orthotitanate; acylates such as hydroxytitanium acetate, hydroxytitanium butyrate or hydroxytitanium pentanoate, or chelates such as tetraethylene glycol titanate or tetrapropylene glycol titanate. It is also possible to successfully use the corresponding zirconium compounds, such as tetra(methyl) orthozirconate, tetra(ethyl) orthozirconate, zirconium carbonate, tetra(propyl) orthozirconate, tetra(isopropyl) orthozirconate, zirconium hydroxide, tetra(butyl) orthozirconate, tetra(isobutyl) orthozirconate, tetra(pentyl) orthozirconate or tetra(2-ethylhexyl) orthozirconate.

Likewise suitable are aluminium oxide, aluminium hydroxide, aluminium carboxylates such as aluminium acetate or aluminium stearate, or aluminium alkoxides such as aluminium tributoxide, aluminium tri-sec-butoxide, aluminium tri-tert-butoxide or aluminium triisopropoxide.

It is also possible to use zinc oxide, zinc sulphate and zinc carboxylates such as zinc acetate dihydrate or zinc stearate, and iron(II) acetate or iron(III) hydroxide oxide, as catalysts.

It is likewise possible to use the appropriate metals in finely divided form, in which case the catalytically active metal compound is first formed within the reaction mixture.

The catalyst can be added to the reaction mixture as early as at the start, or only subsequently with observation of safety measures at elevated temperature, when, for example, the removal of the water of reaction has set in.

The amount of the esterification catalyst added is $1\times10^{-5}$ to 20 mol %, preferably 0.01 to 5 mol %, especially 0.01 to 2 mol %, based on the starting compound added in deficiency, appropriately based on the polyol. In the case of higher amounts of catalyst, cleavage reactions of the polyol esters are to be expected.

In the case of the preparation of polyolesters based on ether diols, for example triethylene glycol or tetraethylene glycol, in the case of use of high catalyst concentrations toward the end of the reaction and in the phase of the conversion of last residues of free hydroxyl groups, there is a risk of enhanced cleavage of the ether chain, such that the reaction temperature or the pressure to be applied should be adjusted in this case. The higher the catalyst concentration selected is, the lower the reaction temperature or the pressure to be applied should generally be selected, and an optimized temperature and pressure profile should be employed. In the case of excessively low catalyst concentrations, the esterification rate becomes so low that an acceptable conversion is not observed within an acceptable reaction time.

The esterification catalyst can be added in liquid or solid form. Solid catalysts, for example tin(II) oxide, zinc oxide or iron(III) hydroxide oxide are filtered off after the esterification reaction has ended, before the crude polyol ester is subjected to the further workup. When the esterification catalysts are added in the form of liquid compounds, for example tetra(isopropyl) orthotitanate or tetra(butyl) orthotitanate, which are still present dissolved in the reaction mixture after the esterification reaction has ended, these compounds are converted in the course of the workup process, in the steam treatment, to insoluble precipitates which can be filtered off readily.

The esterification is effected in the presence of an adsorbent. This involves using porous high-surface area solid materials which are typically used in chemical practice both in the laboratory and in industrial plants. Examples of such materials are high-surface area polysilicic acids such as silica gels (silica xerogels), kieselguhr, high-surface area aluminium oxides and aluminium oxide hydrates, mineral materials such as clays or carbonates, or activated carbon. Activated carbon has been found to be particularly useful. In general, the adsorbent is suspended in finely divided form in the reaction solution, which is agitated by intensive stirring or by introducing an inert gas. This achieves intimate contact between the liquid phase and the adsorbent. The amount of the adsorbent can be adjusted substantially freely and hence according to the individual requirements. Based on 100 parts by weight of the liquid reaction mixture, it is useful to use 0.1 to 5 and preferably 0.1 to 1.5 parts by weight of the adsorbent.

Owing to the quality criteria described at the outset for polyol esters, the process steps in the esterification stage with removal of the water of reaction and in the workup of the crude ester are very important process features, since the adjustment of these process steps influences the sensory and optical properties of the end products to a significant degree. An optimized process regime affords polyol esters based on ether diols, for example triethylene glycol or tetraethylene glycol, with high purity, and also low colour number and high colour stability. The structure of the starting materials, of the polyhydric alcohols and of the aliphatic monocarboxylic acids is, in contrast, crucial for the mechanical and thermal properties of the polymer materials plasticized with the polyol esters, and influences the hydrolysis and oxidation stability of lubricants.

The reaction mixture obtained after the reaction has ended comprises, as well as the polyolester as the desired reaction product, any unconverted starting materials, more particularly aliphatic monocarboxylic acid still in excess, when a monocarboxylic acid excess is employed. Typically, unconverted starting compounds present in excess are first distilled off, appropriately with application of a reduced pressure.

Subsequently, the crude ester is subjected to a treatment with steam, which can be done, for example, in simple form by introducing steam into the crude product. One advantage of steam treatment is that catalyst still present is destroyed in the course thereof and converted to hydrolysis products which can be filtered off readily. Since the esterification reaction is performed in the presence of an adsorbent, the adsorbent already present facilitates the deposition of the catalyst conversion products. The presence of an adsorbent during the steam treatment likewise has an advantageous effect on the colour and on the colour stability of the polyol ester. However, it is also possible to filter off the adsorbent after the esterification reaction has ended and excess starting compounds have been removed, i.e. before performance of the steam distillation.

The steam treatment is generally performed at standard pressure, although the employment of a slightly reduced pressure, appropriately down to 400 hPa, is not ruled out. The steam treatment is effected at temperatures of 150 to 250° C., preferably of 150 to 220° C. and especially of 170 to 200° C., and is also guided by the physical properties of the polyol esters to be prepared in each case.

In the process step of steam treatment, it is found to be appropriate to proceed in a very gentle manner during the heating period until the attainment of the working temperature, in order to heat the crude ester to the required temperature for the steam treatment.

The duration of the steam treatment can be determined by routine tests and it is performed over a period of 0.5 to 5 hours. Too long a steam treatment leads to an undesired increase in the colour number of the polyol ester and should therefore be avoided. An increased degradation reaction of the polyol ester to acidic compounds is also observed, the content of which is manifested in a rise in the neutralization number or acid number, for example determined to DIN EN ISO 3682/ASTM D 1613. In the case of too short a treatment time, the removal of residual acid and water is insufficiently effective, and the desired polyol ester still has too high an undesired acid number and too high a water content. Another observation in the case of too short a treatment time is only a minor advantageous effect on the colour number of the polyol ester.

The conditions in the steam treatment, such as temperature, duration and pressure to be applied, also have to be adjusted precisely to the particular polyol ester, in order to achieve an optimal result in relation to the colour number of the polyol ester and in order to minimize residual contents of starting compounds, water and catalyst traces as far as possible, and simultaneously to suppress degradation reactions. Especially in the case of employment of higher amounts of catalyst and in the case of preparation of polyol esters based on ether diols, for example triethylene glycol or tetraethylene glycol, the conditions in the steam treatment have to be tailored exactly to the particular polyol ester, in order to suppress the undesired degradation of the ether chain.

The steam treatment is optionally followed by the addition of a solid alkaline substance, for example basic silicon dioxide, basic aluminium oxide or sodium carbonate, sodium hydrogencarbonate, calcium carbonate, or sodium hydroxide in solid form, and also basic minerals, in order to further reduce the neutralization number of the polyol ester.

The steam treatment is followed, optionally after filtration of the adsorbent, of any solid alkaline substances added and of further solids obtained, by the drying of the polyol ester, for example by passing an inert gas through the product at elevated temperature. It is also possible to simultaneously apply a reduced pressure at elevated temperature and optionally to pass an inert gas through the product. Even without the action of an inert gas, it is possible to work only at elevated temperature or only under reduced pressure. The particular drying conditions, such as temperature, pressure and time, can be determined by simple preliminary tests. In general, temperatures in the range from 80 to 250° C., preferably 100 to 180° C., are employed at pressures of 0.2 to 500 hPa, preferably 1 to 200 hPa and especially 1 to 20 hPa. Then the crude ester is filtered, if this has not already been done, in order to free it from the solids, any solid alkaline substances added, the hydrolysis products of the catalyst and the adsorbent added in the esterification stage. The filtration is effected in conventional filtering apparatus at standard temperature or at temperatures up to 120° C. The filtration can be supported by common filtration aids such as cellulose, silica gel, kieselguhr, wood flour. However, the use thereof is restricted to exceptional cases.

On completion of the filtration, light-coloured polyol esters are obtained, which generally also satisfy the other specifications, such as water content, residual acid content, residual content of catalyst constituents and residual content of monoester.

The polyol esters to be aftertreated by the process according to the invention are based on polyhydric alcohols corresponding to the general formula $$H-(-O-[-CR^1R^2-]_m-)_o-OH$$

in which $R^1$ and $R^2$ are each independently hydrogen, an alkyl radical having 1 to 5 carbon atoms, preferably methyl, ethyl or propyl, or a hydroxyalkyl radical having 1 to 5 carbon atoms, preferably the hydroxymethyl radical, m is an integer of 1 to 10, preferably 1 to 8 and especially 1, 2, 3 or 4, o is an integer of 2 to 15, preferably 2 to 8 and especially 2, 3, 4 or 5.

Suitable polyols which can be converted to polyol esters are, for example, ditrimethylolpropane, dipentaerythritol and the oligomers of ethylene glycol and 1,2-propylene glycol, especially the ether diols di-, tri- and tetraethylene glycol or dipropylene glycol, tripropylene glycol or tetrapropylene glycol. Ethylene and propylene glycols are industrially produced chemicals. The base substance for preparation thereof is ethylene oxide and propylene oxide, from which 1,2-ethylene glycol and 1,2-propylene glycol are obtained by heating with water under pressure. Diethylene glycol is obtained by ethoxylation from ethylene glycol. Triethylene glycol is obtained, like tetraethylene glycol, as a by-product in the hydrolysis of ethylene oxide to prepare ethylene glycol. Both compounds can also be synthesized by reacting ethylene glycol with ethylene oxide. Dipropylene glycol, tripropylene glycol, tetrapropylene glycol and higher propoxylation products are obtainable from the multiple addition of propylene oxide onto 1,2-propylene glycol.

To obtain polyol esters, linear or branched, aliphatic monocarboxylic acids having 3 to 20 carbon atoms in the molecule are used. Even though preference is given to saturated acids in many cases, depending on the particular field of use of the plasticizers or lubricants, it is also possible to use unsaturated carboxylic acids as a reaction component for ester synthesis. Examples of monocarboxylic acids as components of polyol esters are propionic acid, n-butyric acid, isobutyric acid, n-pentanoic acid, 2-methylbutyric acid, 3-methylbutyric acid, 2-methylpentanoic acid, n-hexanoic acid, 2-ethylbutyric acid, n-heptanoic acid, 2-methylhexanoic acid, cyclohexane-carboxylic acid, 2-ethylhexanoic acid, n-nonanoic acid, 2-methyloctanoic acid, isononanoic acid, 3,5,5-trimethylhexanoic acid, 2-propylheptanoic acid, 2-methylundecanoic acid, isoundecanecarboxylic acid, tricyclodecanecarboxylic acid and isotridecane-carboxylic acid. Of particular significance is the preparation of polyol esters of the oligomeric ethylene glycols and of the oligomeric propylene glycols with $C_4$- to $C_{13}$- or $C_5$- to $C_{10}$-monocarboxylic acids, and for preparation of polyol esters based on ditrimethylolpropane.

The polyol esters of ethylene glycol and the oligomers thereof are outstandingly suitable as plasticizers for all common high molecular weight thermoplastic substances. They have been found to be particularly useful as an additive to polyvinyl butyral which is used admixed with glycol esters as an intermediate layer for production of multilayer or composite glasses. They can likewise be used as coalescence agents or film-forming assistants in aqueous dispersions of polymers which find various uses as coating materials. It is possible to prepare, in a simple manner, polyol esters with outstanding colour properties which also satisfy further quality demands, such as low odour or a low acid number. Particularly processes for preparing triethylene glycol di-2-ethylhexanoate (3G8 Ester), tetraethylene glycol di-n-heptanoate (4G7 Ester), triethylene glycol di-2-ethylbutyrate (3G6 Ester), triethylene glycol di-n-heptanoate (3G7 Ester) or tetraethylene glycol di-2-ethylhexanoate (4G8 Ester) have gained significance.

The esterification of the starting compounds can be performed continuously or batchwise in the reaction apparatus typical for chemical technology. Useful apparatus has been found to be stirred tanks or reaction tubes, the batchwise reaction regime being preferred.

Even though the process according to DE 10 2009 048 775 A1 affords high-quality and on-spec polyol esters, faults in the industrial production can result in polyol esters which do not meet the specification values with regard to the colour number.

According to the inventive procedure, such production batches of polyol esters can be subjected to an aftertreatment in a simple manner, in order to improve the colour quality. For this purpose, the polyol esters obtained are first treated with an oxidizing or reducing compound.

Suitable oxidizing compounds are peroxidic compounds such as hydrogen peroxide, organic percarboxylic acids such as peracetic acid or perpropionic acid, organic hydroperoxides such as cumene hydroperoxide or tert-butyl hydroperoxide, alkali metal or alkaline earth metal perborates, alkali metal or alkaline earth metal percarbonates, alkali metal or alkaline earth metal peroxodisulphates or alkali metal or alkaline earth metal peroxophosphates.

Particularly suitable are aqueous hydrogen peroxide solutions, liquid organic percarboxylic acids or organic hydroperoxides, which can be removed by distillation in a simple manner. The use of the peroxidic alkali metal or alkaline earth metal salt compounds, either in solid form or as an aqueous solution, is not ruled out but it is limited to a few exceptional cases, since they and the reaction products thereof are present as solids or precipitate in the course of the aftertreatment of the polyol ester and have to be removed by an additional filtration step.

Especially suitable for the aftertreatment of the polyol ester which has already been worked up is hydrogen peroxide in the form of an aqueous solution with a hydrogen peroxide content of more than 10% by weight, preferably of 30 to 50% by weight. Hydrogen peroxide solutions with a low active content are not recommended owing to the introduction of an excessive amount of water, which subsequently has to be removed again. In the case of excessive hydrogen peroxide concentrations, inconvenient and costly safety precautions have to be observed in the course of handling.

The peroxidic compound is added to the polyol ester to be treated in such an amount that the active content thereof in the overall mixture is from 0.03 to 1.0% by weight, preferably from 0.08 to 0.3% by weight. In the case of excessively low active concentrations, the decolourizing power is no longer sufficient to obtain light-coloured polyol esters with adequate quality. In the case of excessive active concentrations, uncontrolled degradation reactions of the ester compounds are to be expected.

The treatment with peroxidic compounds is effected generally at elevated temperature, preferably at temperatures of 70 to 160° C., preferably 100 to 120° C., though even low temperatures, for example room temperature or lower, are not ruled out. The treatment time can be selected over a wide range. It should not be too short, but not too long either, and can be determined by simple preliminary tests. In general, the treatment time is 0.5 to 3 hours. In the case of shorter treatment times, no positive effect on the colour number is observed; in the case of excessively long treatment times, there is a risk of increased ester hydrolysis and uncontrolled degradation of the polyol ester structure due to the water present and the oxidizing agent. Likewise, in the event of excessively long treatment times, reactor volume is occupied unnecessarily.

The particular conditions of the treatment with the peroxidic compound should be tailored to the particular polyol ester in order to achieve optimal decolourization on the one hand, but as far as possible to avoid degradation reactions of the polyol ester on the other hand. In the case of polyol esters based on ether diols, for example triethylene glycol or tetraethylene glycol, enhanced degradation of the ether structure can set in when the conditions in the treatment with the peroxidic compound, such as temperature, action time and concentration, are not adjusted specifically to the particular polyol ester.

In a further configuration, the inventive aftertreatment of the polyol esters which have already been worked up to improve the colour quality can be performed with ozone or ozone-containing gases as the oxidizing compound.

For the aftertreatment with ozone or ozone-containing gases, ozone is used in an amount of 0.01 to 5.0 grams, preferably 0.2 to 0.8 gram, per liter of polyol ester. Higher amounts of ozone are not advisable due to the increased onset of degradation reactions of the polyol ester structure. In the event of an excessively high ozone input, in addition to the reduction in the polyol ester content determined by gas chromatography, a rise is also observed in the acid or neutralization number, for example determined to DIN EN ISO 3682/ASTM D 1613, as is an increase in the peroxide number expressed in milliequivalents of oxygen per kilogram of polyol ester and determined, for example, to ASTM E 298. The drift in these characteristics can be inferred with an increased onset of acid formation when an excessively high amount of ozone is used. In the case of excessively low ozone inputs, the advantageous influence on the colour lightening is too minor, or disproportionately long treatment times have to be accepted.

Ozone is used either in pure form or in a mixture with gases, for example with air or oxygen, or in a mixture with inert gases, such as with nitrogen, with carbon dioxide or with the noble gases, such as helium or argon. When ozone-containing gases are used for the treatment, the ozone concentration is appropriately 2 to 200, preferably 10 to 100, grams of ozone per $m^3$ of gas mixture. Preference is given to working with a mixture of ozone in oxygen.

For the production of ozone or ozone-containing gas mixtures, commercially available ozone generators are available, for example instruments designated Ozone Systems SMO Series, PDO Series, SMA Series or PDA Series from ITT Wedeco GmbH.

The treatment with ozone or ozone-containing gases can be effected over a wide temperature range. The lower temperature limit is determined by the viscosity and crystallization properties of the reaction medium, which should be sufficiently pumpable even at low temperatures. At excessively high temperatures, increased onset of decomposition of the ozone is to be expected. For example, it is possible to work over a temperature range from $-30°$ C. up to a temperature of $130°$ C. Preference is given to employing temperatures of 20 to $100°$ C. and especially of 30 to $80°$ C. The treatment time with ozone may likewise extend over a wide range; the oxidizing agent is typically employed over a few minutes up to several hours, for example from one minute up to three hours, preferably from 20 to 90 minutes. Higher temperatures and longer treatment times should be avoided due to an increased onset of decomposition of the ozone and also of the polyol ester. Based on the treatment time, the ozone input should be 0.1 to 5.0, preferably 0.2 to 0.9, grams of ozone per hour and liter of polyol ester.

The particular conditions of the treatment with ozone or ozone-containing gases should be tailored to the particular polyol ester in order to achieve optimal decolourization on the one hand but, on the other hand, to as far as possible avoid degradation reactions of the polyol ester. In the case of polyol esters based on ether diols, for example triethylene glycol or tetraethylene glycol, increased degradation of the ether structure can set in when the conditions in the treatment with ozone or ozone-containing gases, such as temperature, action time or ozone input, are not adjusted specifically to the particular polyol ester.

For the inventive aftertreatment of the polyol esters to improve the colour quality, reducing compounds such as metal hydrides, for example complex alkali metal borohydrides or alkaline earth metal borohydrides, are likewise suitable.

It is appropriate to work with solids, which are first suspended in the polyol ester to be treated and are activated by addition of water. When water is added, reductively active hydrogen is released in situ from the metal hydrides, for example from the complex alkali metal or alkaline earth metal borohydrides. The input of excessively high amounts of water should be avoided since the water subsequently has to be removed again, and excessively high amounts of water also cause excessively rapid deactivation of the active hydrogen compounds formed in situ. In general, based on 100 parts by weight of polyol ester to be aftertreated, from 0.1 to 5.0 parts by weight, preferably from 0.1 to 2.0 parts by weight, of water are used.

The reducing compound is added to the polyol ester to be treated in such an amount that the active content thereof in the overall mixture of polyol ester and added water is from 0.002 to 0.3% by weight, preferably from 0.005 to 0.05% by weight. In the case of excessively low active concentrations, the decolourizing power is no longer sufficient to obtain light-coloured polyol esters with sufficient quality. In the case of excessively high active concentrations, uncontrolled degradation reactions of the ester compounds are to be expected.

The treatment with reducing compounds is effected generally at elevated temperature, preferably at temperatures of 70 to $160°$ C., preferably 80 to $120°$ C., though low temperatures, for example room temperature or lower, are also not ruled out. The treatment time can be selected over a wide range. It should not be too short, but not too long either, and can be determined by simple preliminary tests. In general, the treatment time is 0.5 to 3 hours. In the case of shorter treatment times, no positive influence on the colour number is observed; in the case of excessively long treatment times, there is a risk of increased ester hydrolysis and uncontrolled degradation of the polyol ester structure due to the presence of water and to the reducing compound. Likewise, in the case of excessively long treatment times, reactor volume is occupied unnecessarily.

The particular conditions of the treatment with the reducing compound should be tailored to the particular polyol ester in order to achieve optimal decolourization on the one hand, but as far as possible to avoid degradation reactions of the polyol ester on the other hand. In the case of polyol esters based on ether diols, for example triethylene glycol or tetraethylene glycol, increased degradation of the ether structure can set in when the conditions in the treatment with the reducing compound, such as temperature, action time and concentration, are not adjusted specifically to the particular polyol ester.

After the oxidative or reductive aftertreatment, the polyol ester, without further intermediate steps, is immediately thereafter subjected to a treatment with steam, which can be effected, for example, in simple form by introducing steam. One advantage of the steam treatment is that excess oxidizing or reducing compounds are destroyed in the course thereof, and the water introduced is removed with the steam.

The steam treatment is generally performed at standard pressure, although the employment of a slightly reduced pressure, appropriately down to 400 hPa, is not ruled out. The steam treatment is performed at temperatures of 150 to 250° C., preferably of 150 to 220° C. and especially of 170 to 200° C., and is also guided by the physical properties of the polyol esters to be prepared in each case.

In the process step of steam treatment, it is found to be appropriate to proceed very gently during the heating period until the attainment of the working temperature, in order to heat the mixture of polyol ester and added oxidizing or reducing compound to the temperature required for the steam treatment.

The duration of the steam treatment can be determined by routine tests, and it is performed over a period of 0.5 to 5 hours. An excessively long steam treatment leads to an unwanted increase in the colour number of the polyol ester and should therefore be avoided. Also observed is an enhanced degradation reaction of the polyol ester to give acidic compounds, the content of which is manifested in a rise in the neutralization number or acid number, for example determined to DIN EN ISO 3682/ASTM D 1613. In the case of an excessively short treatment time, the destruction of the excess oxidizing compound is incomplete, and the desired polyol ester in the case of the aftertreatment with an oxidizing compound still has an excessively high unwanted peroxide number, expressed in milliequivalents of oxygen per kilogram of product and determined to ASTM E 298. Also in the case of an excessively short treatment time, only a minor advantageous effect is observed on the colour number of the polyol ester.

As in the treatment with the oxidizing or reducing compound, the conditions in the immediately subsequent steam treatment too, such as temperature, pressure and duration, should be adjusted specifically to the particular polyol ester in order to achieve an optimal result in relation to the colour number of the polyol ester and to minimise residual contents of water introduced and of peroxide traces, and at the same time to suppress degradation reactions. In the case of polyol esters based on ether diols, for example triethylene glycol or tetraethylene glycol, the conditions in the steam treatment should be exactly tailored to the particular polyol ester in order to prevent the unwanted degradation of the ether chain.

In general, after the steam treatment, an on-spec polyol ester is obtained, and further aftertreatment steps, such as an additional drying, are dispensable but are not ruled out.

When metal hydrides or alkali metal or alkaline earth metal borohydrides are employed as the reducing compound, it is found to be appropriate to perform the steam treatment in the presence of an alkaline compound, for example with sodium hydroxide or sodium carbonate, either in solid form or as an aqueous solution. Based on one equivalent of the acid derived from the metal or boron, 1.2 to 1.5 equivalents of alkaline compound are added.

After the steam treatment, metal-containing or boron-containing solids are obtained. In these cases, the steam treatment is immediately followed, without further intermediate steps, by the drying of the aftertreated polyol ester, for example by passing an inert gas through the product at elevated temperature. It is also possible to simultaneously apply a reduced pressure at elevated temperature, and optionally to pass an inert gas through the product. Even without the action of an inert gas, it is possible to work only at elevated temperature or only at lower pressure. The particular drying conditions, such as temperature, pressure and duration, can be determined by simple preliminary tests and should be tailored to the particular polyol ester. In general, the temperatures employed are in the range from 80 to 250° C., preferably 100 to 180° C., and the pressures employed are from 0.2 to 500 hPa, preferably 1 to 200 hPa and especially 1 to 20 hPa. After the drying has ended, metal-containing or boron-containing solids deposited, which have formed during the steam treatment or during the drying, are filtered off.

The inventive aftertreatment of polyol esters can remedy colour problems when the industrial production according to the process of DE 10 2009 048 775 A1 gives rise to production batches which are off-spec with regard to the colour number required.

The examples which follow illustrate the process according to the invention in detail, but it is not restricted to the embodiment described.

WORKING EXAMPLES

Comparative Examples

For the experiments for colour lightening, catalytically prepared triethylene glycol di-2-ethylhexanoate with a colour number of 37 Hazen units was used, which had been obtained with the aid of a titanium catalyst by esterification of triethylene glycol with a 2.6 molar amount of 2-ethylhexanoic acid. The catalyst concentration was 0.05 mol %, based on triethylene glycol used. The content (% by weight), determined by gas chromatography, of triethylene glycol di-2-ethylhexanoate was 97.9%, that of triethylene glycol mono-2-ethylhexanoate 1.0%, and the remainder to 100% was 1.1%.

Example 1 for Aftertreatment

An aftertreatment for lightening the colour of the catalytically prepared triethylene glycol di-2-ethylhexanoate with an aqueous hydrogen peroxide solution was effected under the following conditions:

| | |
|---|---|
| Concentration of aqueous $H_2O_2$ solution | 30% by weight |
| Amounts of $H_2O_2$, absolute based on the overall reaction mixture | 0.10% by weight |
| Reaction temperature | 120° C. |
| Reaction time | 2 hours |

The immediately subsequent steam distillation was performed under the following conditions:

| | |
|---|---|
| Working temperature of the steam distillation | 180° C. |
| Treatment time | 1 hour |

The subsequent drying was performed under the following conditions:

| | |
|---|---|
| Pressure | 10 hPa |
| Drying temperature | 80° C. |
| Drying time | 1 hour |

On completion of the workup, a light-coloured polyol ester was obtained with the following contents determined by gas chromatography:

| | |
|---|---|
| Triethylene glycol di-2-ethylhexanoate content | 97.6% by weight |
| Triethylene glycol mono-2-ethylhexanoate content | 1.0% by weight |
| Remainder | 1.4% by weight | and the following characteristics:

| | |
|---|---|
| Hazen colour number (DIN ISO 6271) | 11 |
| Neutralization number (mg KOH/g, DIN EN ISO 3682/ASTM D 1613) | 0.06 |
| Water content (% by weight, DIN 51777 part 1) | 0.02 |
| Peroxide content (meq O/kg, ASTM E 298) | 0.9 |

Example 2 for Aftertreatment

The aftertreatment of the triethylene glycol di-2-ethylhexanoate was performed with in each case 1 liter of crude product in a heatable 2 liter four-neck flask which was equipped with a stirrer, internal thermometer and feed line with a bead frit of pore size G3. In the ITT Wedeco GmbH Modular 8HC (BHT 964) ozone generator, an ozone-containing oxygen stream was generated with an ozone concentration of 21 grams of ozone per cubic meter of oxygen, which was passed at a rate of 0.025 m$^3$/hour via the bead frit through the crude ester at a temperature of 70° C. over a period of 0.5 hour while stirring vigorously.

For the subsequent steam distillation, the ozone feed line was replaced by a distillation apparatus with a 1 liter receiver, and the 2 liter four-neck flask was equipped with an immersed tube for passage of steam.

After performance of the steam distillation under the conditions described below, the supply of steam was stopped and a reduced pressure was applied over the distillation apparatus for final drying. The residue obtained was a light-coloured, on-spec polyol ester.

The steam distillation which immediately followed the ozone treatment was performed under the following conditions:

| | |
|---|---|
| Working temperature of the steam distillation | 180° C. |
| Treatment time | 1 hour |

Subsequently, the following drying conditions were established:

| | |
|---|---|
| Pressure | 10 hPa |
| Drying temperature | 80° C. |
| Drying time | 1 hour |

On completion of the workup, a light-coloured polyol ester was obtained with the following contents determined by gas chromatography:

| | |
|---|---|
| Triethylene glycol di-2-ethylhexanoate content | 97.5% by weight |
| Triethylene glycol mono-2-ethylhexanoate content | 1.0% by weight |
| Remainder | 1.5% by weight | and the following characteristics:

| | |
|---|---|
| Hazen colour number (DIN ISO 6271) | 12 |
| Neutralization number (mg KOH/g, DIN EN ISO 3682/ASTM D 1613) | 0.06 |
| Water content (% by weight, DIN 51777 part 1) | 0.03 |
| Peroxide content (meq O/kg, ASTM E 298) | 1.15 |

Example 3 for Aftertreatment

An aftertreatment for lightening the colour of the catalytically prepared triethylene glycol di-2-ethylhexanoate with sodium borohydride was effected under the following conditions:

| | |
|---|---|
| Amount of water added per 100 parts by weight of polyol ester | 1.5 parts by weight |
| Concentration of NaBH$_4$ | 150 ppm |
| Reaction temperature | 120° C. |
| Reaction time | 2 hours |

The steam treatment which immediately followed the sodium borohydride treatment was effected under the following conditions:

| | |
|---|---|
| Addition of solid sodium carbonate | 1.2 equivalents per 1 equivalent of boric acid |
| Working temperature of the steam distillation | 180° C. |
| Treatment time | 1 hour |

The subsequent drying was performed under the following conditions:

| | |
|---|---|
| Pressure | 10 hPa |
| Drying temperature | 80° C. |
| Drying time | 1 hour |

On completion of the workup and filtration, a light-coloured polyol ester was obtained with the following contents determined by gas chromatography:

| | |
|---|---|
| Triethylene glycol di-2-ethylhexanoate content | 97.3% by weight |
| Triethylene glycol mono-2-ethylhexanoate content | 1.1% by weight |
| Remainder | 1.6% by weight | and the following characteristics:

| | |
|---|---|
| Hazen colour number (DIN ISO 6271) | 19 |
| Neutralization number (mg KOH/g, DIN EN ISO 3682/ASTM D 1613) | 0.08 |
| Water content (% by weight, DIN 51777 part 1) | 0.03 |

The invention claimed is:

1. Process for aftertreatment of polyol esters prepared by reacting polyols of the general formula

in which $R^1$ and $R^2$ are each independently hydrogen, an alkyl radical having 1 to 5 carbon atoms, or a hydroxyalkyl radical having 1 to 5 carbon atoms, m is an integer from 1 to 10, o is an integer from 2 to 15, with linear or branched aliphatic monocarboxylic acids having 3 to 20 carbon atoms in the presence of an adsorbent and in the presence of metal compounds selected from the group of titanium compounds, zirconium compounds, tin compounds, zinc compounds, iron compounds and aluminium compounds as a catalyst while removing the water formed and subsequently treating with steam, characterized in that the polyol ester obtained is aftertreated first with an oxidizing or reducing compound and immediately thereafter with steam at a temperature of 150 to 250° C. and over a period of 0.5 to 5 hours, wherein the first aftertreatment with an oxidizing or reducing compound is carried out at a temperature of from 20 to 100° C.

2. Process according to claim 1, in which $R^1$ and $R^2$ are each independently methyl, ethyl or propyl.

3. Process according to claim 1, in which $R^1$ and $R^2$ are the hydroxymethyl radical.

4. Process according to claim 1, in which m is an integer from 1 to 8.

5. Process according to claim 1, in which m is 1, 2, 3 or 4.

6. Process according to claim 1, in which o is an integer from 2 to 8.

7. Process according to claim 1, in which o is 2, 3, 4, or 5.

8. Process according to claim 1, characterized in that the oxidizing compounds used are peroxidic compounds.

9. Process according to claim 8, characterized in that the peroxidic compounds used are hydrogen peroxide, peracetic acid, perpropionic acid, cumene hydroperoxide, tert-butyl hydroperoxide, alkali metal or alkaline earth metal perborates, alkali metal or alkaline earth metal percarbonates, alkali metal or alkaline earth metal peroxodisulphates or alkali metal or alkaline earth metal peroxophosphates.

10. Process according to claim 9, characterized in that hydrogen peroxide is used in the form of an aqueous solution.

11. Process according to claim 1, characterized in that the oxidizing compound used is ozone or ozone-containing gases.

12. Process according to claim 11, characterized in that mixtures of ozone and oxygen are used.

13. Process according to claim 1, characterized in that the reducing compounds used are metal hydrides, especially complex alkali metal borohydrides or alkaline earth metal borohydrides.

14. Process according to claim 13, characterized in that water is added during the use of metal hydrides and the immediately subsequent treatment with steam is effected in the presence of an alkaline compound.

15. Process according to claim 1, characterized in that the steam treatment is followed by drying and filtration.

16. Process according to claim 1, characterized in that the polyols used are ditrimethylolpropane, dipentaerythritol, diethylene glycol, triethylene glycol, tetraethylene glycol, dipropylene glycol, tripropylene glycol or tetrapropylene glycol.

17. Process according to claim 1, characterized in that the aliphatic monocarboxylic acid converted is propionic acid, n-butyric acid, isobutyric acid, n-pentanoic acid, 2-methylbutyric acid, 3-methylbutyric acid, 2-methylpentanoic acid, n-hexanoic acid, 2-ethylbutyric acid, n-heptanoic acid, 2-methylhexanoic acid, 2-ethylhexanoic acid, n-nonanoic acid, 2-methyloctanoic acid, isononanoic acid, 3,5,5-trimethylhexanoic acid or 2-propylheptanoic acid.

18. Process according to claim 1, for aftertreatment of triethylene glycol di-2-ethylhexanoate, tetraethylene glycol di-n-heptanoate, triethylene glycol di-2-ethylbutyrate, triethylene glycol di-n-heptanoate or tetraethylene glycol di-2-ethylhexanoate.

19. Process according to claim 1, wherein the adsorbent present during the reaction of the polyols with monocarboxylic acids is present in an amount of from 0.1 to 5 parts by weight per 100 parts by weight of reaction mixture.

20. Process according to claim 19, wherein the adsorbent is selected from:
polysilicic acids; kieselguhr; aluminum oxides; aluminum oxide hydrates; and clay or carbonate minerals.

21. Process for aftertreatment of polyol esters prepared by reacting polyols of the general formula

in which $R^1$ and $R^2$ are each independently hydrogen, an alkyl radical having 1 to 5 carbon atoms, or a hydroxyalkyl radical having 1 to 5 carbon atoms, m is an integer from 1 to 10, o is an integer from 2 to 15, with linear or branched aliphatic monocarboxylic acids having 3 to 20 carbon atoms in the presence of an adsorbent and in the presence of metal compounds selected from the group of titanium compounds, zirconium compounds, tin compounds, zinc compounds, iron compounds and aluminium compounds as a catalyst while removing the water formed and subsequently treating with steam, characterized in that the polyol ester obtained is aftertreated first with an oxidizing compound selected from hydrogen peroxide, alkali metal or alkaline earth metal perborates, alkali metal or alkaline earth metal percarbonates, alkali metal or alkaline earth metal peroxodisulphates or alkali metal or alkaline earth metal peroxophosphates, ozone and ozone-containing gases or reducing compound and immediately thereafter with steam at a temperature of 150 to 250° C. and over a period of 0.5 to 5 hours, wherein the first aftertreatment with an oxidizing or reducing compound is carried out at a temperature of from 20 to 100° C.

* * * * *